United States Patent [19]

Muchisky et al.

[11] Patent Number: 4,595,196

[45] Date of Patent: Jun. 17, 1986

[54] INCENTIVE SPIROMETER

[76] Inventors: Thomas P. Muchisky, 784 Hawthicket La., Des Peres, Mo. 63131; James V. Young, 35 Benton Pl., St. Louis, Mo. 63104

[21] Appl. No.: 541,355

[22] Filed: Oct. 13, 1983

[51] Int. Cl.⁴ .......................... A63B 23/00; A61B 5/08
[52] U.S. Cl. ....................................... 272/99; 128/721
[58] Field of Search .................. 272/99; 128/716, 721, 128/725

[56] References Cited

U.S. PATENT DOCUMENTS

| | | | |
|---|---|---|---|
| 443,204 | 12/1890 | Davis | 272/99 X |
| 1,055,267 | 3/1913 | Gibson | 272/99 X |
| 1,074,846 | 10/1913 | Dickman | 272/99 X |
| 1,134,320 | 4/1915 | Drew | 128/721 |
| 2,428,980 | 10/1947 | McCann | 128/721 |
| 2,541,562 | 2/1951 | Villarreal | 128/721 |
| 3,097,639 | 7/1963 | Streimer | 128/721 |
| 3,268,845 | 8/1966 | Whitmore | 128/721 |
| 3,483,861 | 12/1969 | Tiep | 128/721 |
| 3,782,368 | 1/1974 | Reibold | 128/721 |

FOREIGN PATENT DOCUMENTS

| | | | |
|---|---|---|---|
| 1124631 | of 1962 | Fed. Rep. of Germany | 128/721 |
| 2148115 | 6/1973 | Fed. Rep. of Germany | 128/721 |
| 329502 | of 1935 | Italy | 128/721 |
| 413628 | of 1946 | Italy | 128/721 |

*Primary Examiner*—Kyle L. Howell
*Assistant Examiner*—John C. Hanley
*Attorney, Agent, or Firm*—Polster, Polster and Lucchesi

[57] ABSTRACT

A deep breathing exercise device includes a belt member to be positioned around the lower chest wall, with the belt ends joined by a plastic case, one end of the belt being mounted to the case by a negatively-variable-resistance leaf spring permitting limited withdrawal of the belt end from within the case, the case having a plurality of LEDs and a chime to indicate movement of the belt from within the case as the circumferential length of the belt system increases in response to an inhaling motion of the wearer.

5 Claims, 6 Drawing Figures

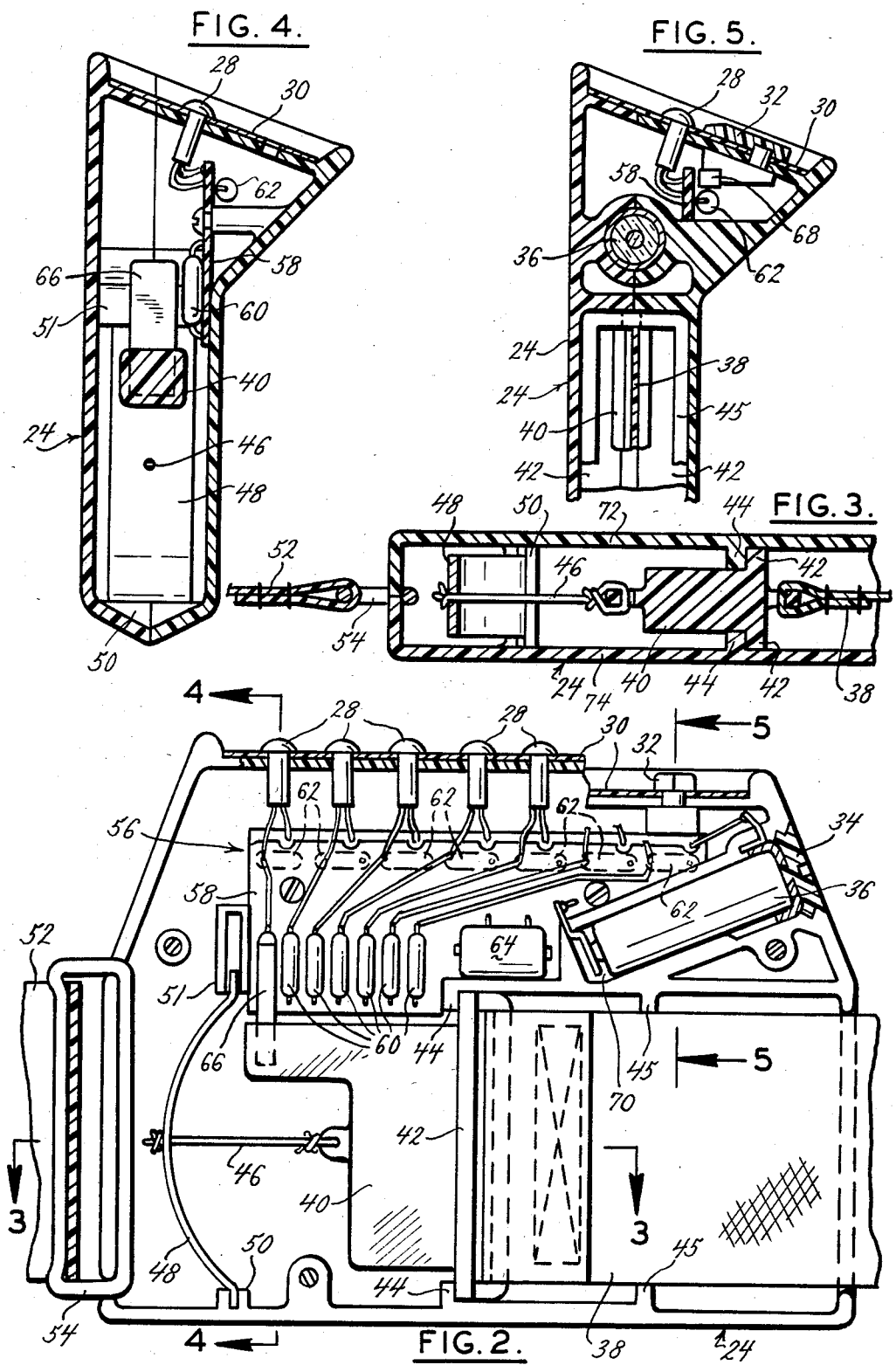

INCENTIVE SPIROMETER

BACKGROUND AND SUMMARY

Regular deep breathing exercises are commonly prescribed for patients following any significant chest or abdominal surgery, to minimize the incidence of pulmonary complications. Pain, analgesics, and the patients' fear of re-opening an incision produces a change in the patients' normal pattern of breathing, and as a result, deep inspiration often fails to occur postoperatively unless the patient is encouraged to participate in deep-inspiration exercises, or is forced to do so through mechanically-controlled inhalation therapy machines. Various self-use mechanical devices are also frequently used in deep-breathing exercises. Many of these devices additionally provide biofeedback and monitor the patient's progress. These devices are generally referred to as "incentive spirometers". However, these self-use devices monitor *total* volume of air in the lungs and do not encourage nor monitor the specific contraction and expansion of the *lower* lobes of the lung, which are *most* susceptible to *infection*. Specific exercising of the *lower* lobes of the lungs is critical for proper respiratory exercise, to minimize the onset of pulmonary disease, such as pneumonia or atelectasis. This is because fluids tend to accumulate in the *lower* lobes of the lungs, and exercise of only the upper lung areas encourages this migration of fluids. The prior art devices are not highly effective in achieving expansion and contraction of specific *lower* lung areas, as patients have a tendency to cheat to avoid the discomfort and pain associated with lower-lobe exercise.

For example, patients can defeat the purpose of many of the prior art devices by using their upper chest only, or by narrowing their lips to increase the measured air flow rate, or by not starting each exhalation with a fully-expanded chest, or each inhalation with a fully-contracted chest. To avoid this cheating, and to compensate for the deficiency of the prior art self-use devices, therapists sit in front of their patient, place their hands on and around the patient's *lower* chest, with thumbs touching after the patient has fully-exhaled. The therapist then requires the patient to cause the therapists' thumbs to move apart by requiring the patient to physically expand his *lower* chest cavity. This technique does achieve the desired result, but requires a therapist to administer the exercise, and does not lend itself to *self* exercise either in the hospital or at home.

To meet this need for an incentive spirometer which: (1) encourages the exercise of the *lower* portions of the lungs; (2) provides biofeedback to the patient to encourage a regular exercise activity, and, more importantly; (3) can be successfully and effectively used by the patient himself in an unsupervised environment, the inventors herein have succeeded in developing an incentive spirometer which includes a non-elastic belt of an adjustable length which can be secured firmly about the patient's lower chest, and which has a unique fastener joining the belt ends to provide a measured expansion of the belt as the lower chest only expands and to graphically indicate to the patient his progress in the exercise routine. To achieve this, one end of the belt is secured to a leaf spring inside the fastener, the leaf spring resisting withdrawal of that belt end from the fastener. Since a patient's ability to expand his lungs is greatest when his lungs are in their minimal expansion phase, the resistive mechanism within the fastener provides maximum resistance when the lungs are in their minimal expansion phase, with the resistive mechanism providing gradually decreasing resistance as the lungs expand, and gradually increasing resistance as the lungs contract.

A series of LEDs are progressively lighted to indicate the withdrawal of the belt, and a chime may also be preset to audibly sound after the belt has reached a designated position. The chime can be adjusted for different amounts of travel as the patient progresses with his exercise routine, and will always give a clear indication of the point at which the patient can relax. Additionally a numerical counter can be provided to count the total repetitions completed. Since the biofeedback mechanism provided by the LEDs and chime is adjustable, the incentive spirometer of the present invention can be used to provide a progressive developmental program of lower-lung exercise which can be visibly followed by the patient and/or therapist as either or both observe the LEDs being illuminated to indicate a greater expansion of the lower portion of his lungs. The progressive developmental program can be varied by increasing or decreasing both the required degree of expansion necessary to activate a pre-set LED and/or the number of required repetitions, as pre-established by the therapist.

The first LED is used to indicate the proper degree of belt tension; as the belt is fastened firmly around the user, the first LED is activated thus signalling to the user that the belt is fastened with a proper degree of tension. The first LED is a different color than the sequential LEDs which monitor lower lung expansion. This system provides the *same* degree of belt tension regardless of body size.

As these exercises can be uncomfortable, or even painful depending upon the surgery, it is important that the device create some interest for the patient, and possibly even capture his curiosity and fascinate him to encourage him to continue the exercise program. With the present invention, the successive flashing of the LEDs as the belt is withdrawn is visually attractive, and the chime which sounds at the end of the exercise is an audible reward for completing an exercise repetition to provide a sense of achievement and satisfaction. In some senses, the visual and audio feedback parallels that experienced through the playing of the various electronic games presently in vogue. If the optional counter is incorporated, even greater incentive is established.

Another important feature of the invention is the leaf spring which secures one end of the belt to the fastener. The leaf spring is of a negator type which provides a greater resistance upon initial deflection with a lessening resistance as the spring is further deflected. Thus, the greatest resistance is provided as the patient *first* starts to inhale, and a lesser resistance as the patient reaches the *end* of his inhalation motion. A most important feature of the invention is that the reverse is accordingly also achieved: as the patient *exhales,* belt resistance *increases,* helping to force as much air as possible *out* of the lower lobes of the lung, thereby assisting in the mobilization of accumulated fluids out of the lungs. These two resistive forces (decreasing resistance during inhalation; increasing resistance during exhalation) are currently produced with manual pressure by a therapist, in response to the anatomical strength of the muscles of the diaphragm, which becomes less effective as they reach the limits of their range of motion. The fastener may be constructed by plastic injection molding techniques, and easily assembled to minimize cost and make the incentive spirometer affordable to almost any patient for use at home. Adjustment of the belt is achieved through a swingable loop through which an end of the belt is inserted and then secured with suitable Velcro TM material.

These and other features and benefits of the incentive spirometer disclosed herein may be more fully appreciated by referring to the drawings and description of the preferred embodiment which follows.

BRIEF DESCRIPTION OF THE DRAWINGS

FIG. 2 is a cross sectional view of the fastening member taken along the plane of line 2—2 in FIG. 1 and detailing its internal construction.

FIG. 3 is a cross sectional view taken along the plane of line 3—3 in FIG. 2 and detailing the mounting of the two belt ends to the fastener.

FIG. 4 is a cross sectional view taken along the plane of line 4—4 in FIG. 2 and detailing the mounting of a switch, the switch acuator, and one of the LEDs.

FIG. 5 is a cross sectional view taken along the plane of line 5—5 in FIG. 2 detailing the adjustable actuator for the chime.

DETAILED DESCRIPTION OF THE PREFERRED EMBODIMENT

Figure 1:
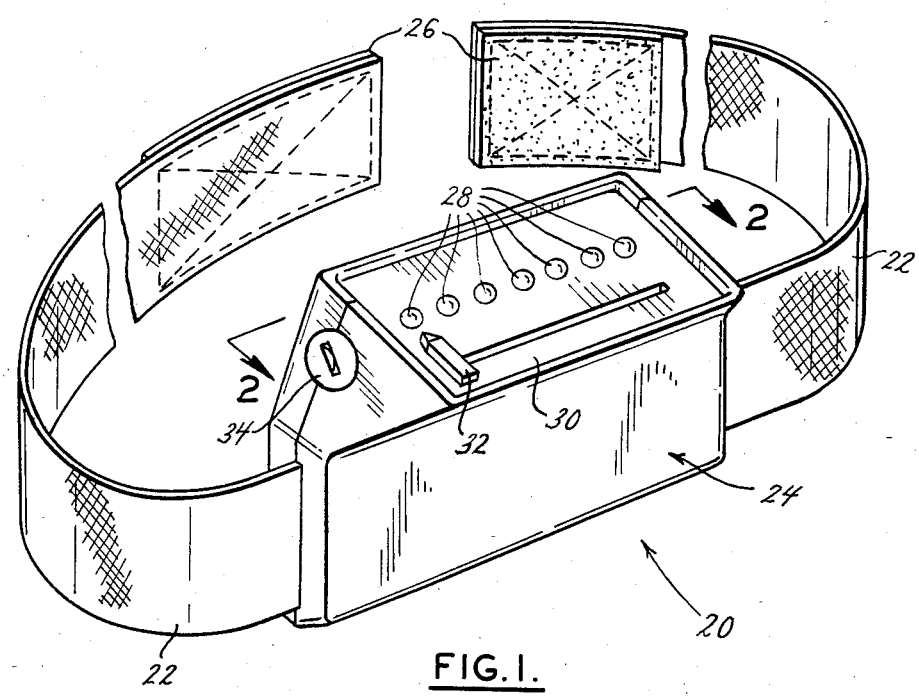
FIG. 1 is an isometric view of the incentive spirometer.

The incentive spirometer 20 of the present invention includes a belt member 22 and a fastening member 24, as shown in FIG. 1. Velcro fastening material 26 is sewn along the ends of belt member 22 to permit fastening of the belt member 22 about the torso. A plurality of LEDs 28 are spaced along the upper face 30 of joining member 24, and light sequentially as the belt 22 is withdrawn from within the joining member 24. This is explained in greater detail below. A slidable indicator 32 provides an adjustment for the point at which an audible signal is given. A circular cover plate 34 may be removed for the installation of a battery 36 to power the electrical circuits contained within joining member 24.

The interior of joining member 24 is shown in greater detail in FIG. 2 wherein the belt 22 has one end 38 secured to a guide member 40, the guide member 40 has a stop portion 42 which abuts a pair of opposed flanges 44 to limit the inward extension of belt member end 38. A second set of opposed flanges 45 (shown in FIG. 2) limit the outward movement of belt member end 38. A flexible cord 46 connects the other end of guide member 40 to a leaf spring 48 of the negator type, one end of leaf spring 48 being secured by spring mount 50 to the interior of joining member 24. The other end of spring 48 is slidably mounted in an elongated track 51 which permits it to move as the belt 22 is withdrawn to deflect spring 48. The other belt end 52 is secured to a swingable strap mount 54 which loosely mounts belt end 52 to the side of joining member 24. The electronic circuit 56 included in joining member is physically mounted on a PC board 58 and includes a plurality of proximity switches 60 on the front of the board, a second plurality of proximity switches 62 mounted on the rear of the board, and a chime 64 mounted on the front face of the board. A rectangular shaped permanent magnet 66 is secured to guide member 40 to operate the first plurality of proximity switches 60, A second permanent magnet 68 is mount to the slidable indicator 32 to operate the second plurality of proximity switches 62. The battery 36 is contained in a cylindrical battery holder 70 with circular cover plate 34 holding battery 36 in place.

As shown in FIG. 3, guide member 40 is physically limited by the walls 72, 74 of joining member 24 such that it moves linearly within joining member 24. The flexible cord 46 joining guide member 40 to negator leaf spring 48 also insures this linear movement. The stop portion of guide member 40 abuts the flanges 44 as the leaf spring 48 seats the guide member 44, and hence belt end 38 within the joining member 24.

As shown in FIG. 4, rectangular permanent magnet 66 is rigidly secured to guide member 40 and is closely adjacent the first plurality of proximity switches 60 mounted on PC board 58. The controlled linear movement of guide member 40 insures that proximity switches 60 are accurately operated by maintaining the proper spacing with permanent magnet 66.

As shown in FIG. 5, the second permanent magnet 68 is mounted on the slidable indicator 32, and closely adjacent the second plurality of proximity switches 62. The physical mounting of slidable indicator 32 to the joining member 24 insures that this minimum spacing is maintained as the indicator 32 is moved along the base 30 to adjust the position at which chime 64 is operated.

Figure 6:
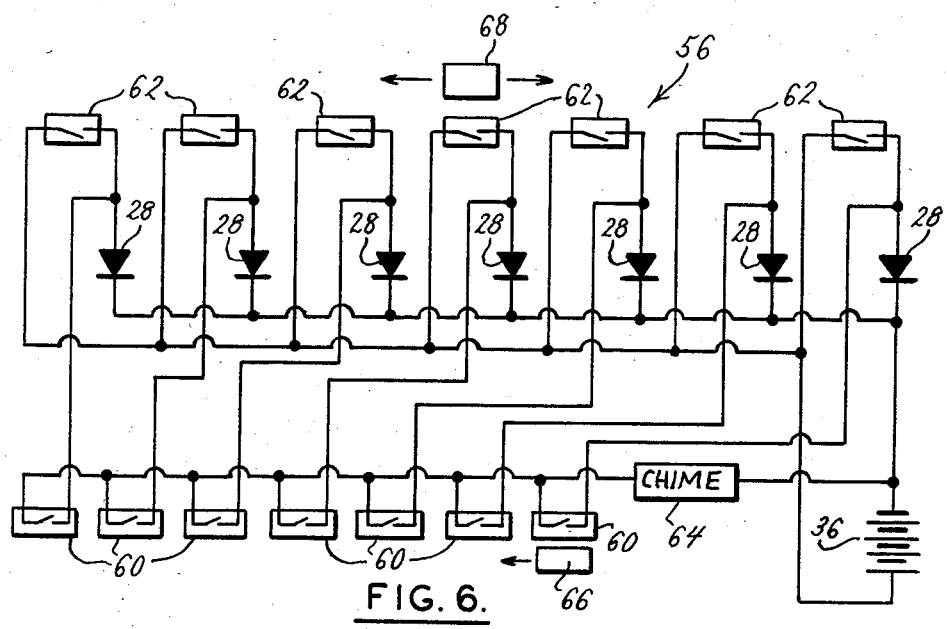
FIG. 6 is an electrical schematic showing the acuator switches, LEDs, chime, and permanent magnet operators.

Referring now to the electrical schematic of FIG. 6, battery 36 supplies power to one side of each of the first plurality of proximity switches 60 operated by first permanent magnet 66. LEDs 28 are connected in circuit with this first plurality of proximity switches 60, the output of which is connected to the other side of battery 36. Each proximity switch 60 has its output connected to the input side of a corresponding proximity switch 62 in the second plurality. The second plurality of proximity switches 62 is operated by the second permanent magnet 68, the outputs of which are connected to chime 64 and the other side of battery 36. In operation, the slidable indicator 32 is adjusted to the desired location for operation of chime 64, thus positioning permanent magnet 68 adjacent a corresponding proximity switch 62 and closing it through electromagnetic forces. The belt 22 is fastened snugly about the patient's lower chest until the first LED (which may be of a different color) is illuminated, and the belt is then fixed in position by the Velcro TM fastener. Then, after the belt 22 is expanded by the patient, permanent magnet 66 moves from one side of the electrical schematic depicted in FIG. 6 to the other to successively operate the LEDs 28. When the proximity switch 60 whose output is connected to the selected proximity switch 62 is operated, chime 64 is operated to sound an audible signal. This provides feedback to the user of the incentive spirometer 20 to indicate that he has expanded the belt 22 the predetermined distance.

There are various changes and modifications which may be made to applicant's invention as would be apparent to those skilled in the art. However, any of these changes or modifications are included in the teaching of applicant's disclosure and he intends that his invention be limited only by the scope of the claims appended hereto. Such aforementioned modifications might include: solid state electronics, alternate "spring" configurations or other gradually-increasing/decreasing-resistance mechanisms for the variable resistance feature; a lower-cost model which eliminates the chime and/or digital counter; a variation in total number of LEDs; a positively-increasing-resistance mechanism for certain prescribed exercise therapies; an elastic or pneumatic belt for other prescribed exercise therapies; alternate surface development configurations, etc.

What is claimed is:

1. A breathing exercise device comprising:
a belt having first and second ends,
a joining member for joining the ends of said belt;
means attached to said joining member for permitting limited relative movement between said belt ends, whereby the belt can be placed around a lower chest and expand with the chest, wherein said means for permitting further includes means for resisting separation of said belt ends, wherein said means for resisting comprises a curved leaf spring having first and second ends mounted on said joining member wherein at least one end of said spring is slidably mounted in such a way as to permit straightening of the curved spring; wherein said first end of said belt is connected to the joining member and said second end of said belt is slidably mounted on the joining member and further secured to a portion of said spring intermediate and means for measuring and indicating the relative separation between the ends of the belt.

2. The device of claim 1 wherein said measuring means includes a magnet secured to said second belt end and a plurality of spaced magnetically actuated proximity switches mounted on said joining member adjacent to said second belt end in such a position so as to be respectively actuated by the magnet in response to various degrees of sliding movement of the second end of the belt with respect to the joining member; and said indicating means includes a plurality of LED's and means for energizing a respective individual LED corresponding to a respectively actuated proximity switch.

3. The device of claim 2, wherein the LED indicator corresponding to the smallest separation of said belt ends has a different color indication than the other LED's in said indication means, whereby the belt can be initially adjusted to provide a predetermined degree of belt tension.

4. The device of claim 1 wherein said indicating means further includes a chime and an adjustable indicator means for causing said chime to sound in accordance with actuation of a selected proximity switch in said measuring means, whereby the chime can be set to sound when a predetermined degree of chest expansion is achieved.

5. The device of claim 4 wherein said adjustable indicator means includes a plurality of spaced magnetically actuated proximity switches, each of which is in circuit with a respective magnetically actuated proximity switch in said measuring means and in circuit with said chime, and a second magnet slidably positioned on said joining member, whereby the second magnet can be selectively positioned to close a selected switch in said adjustable indicator means so that the chime will sound in response to actuation of a selected proximity switch in the means for measuring.

* * * * *